Figure 1:
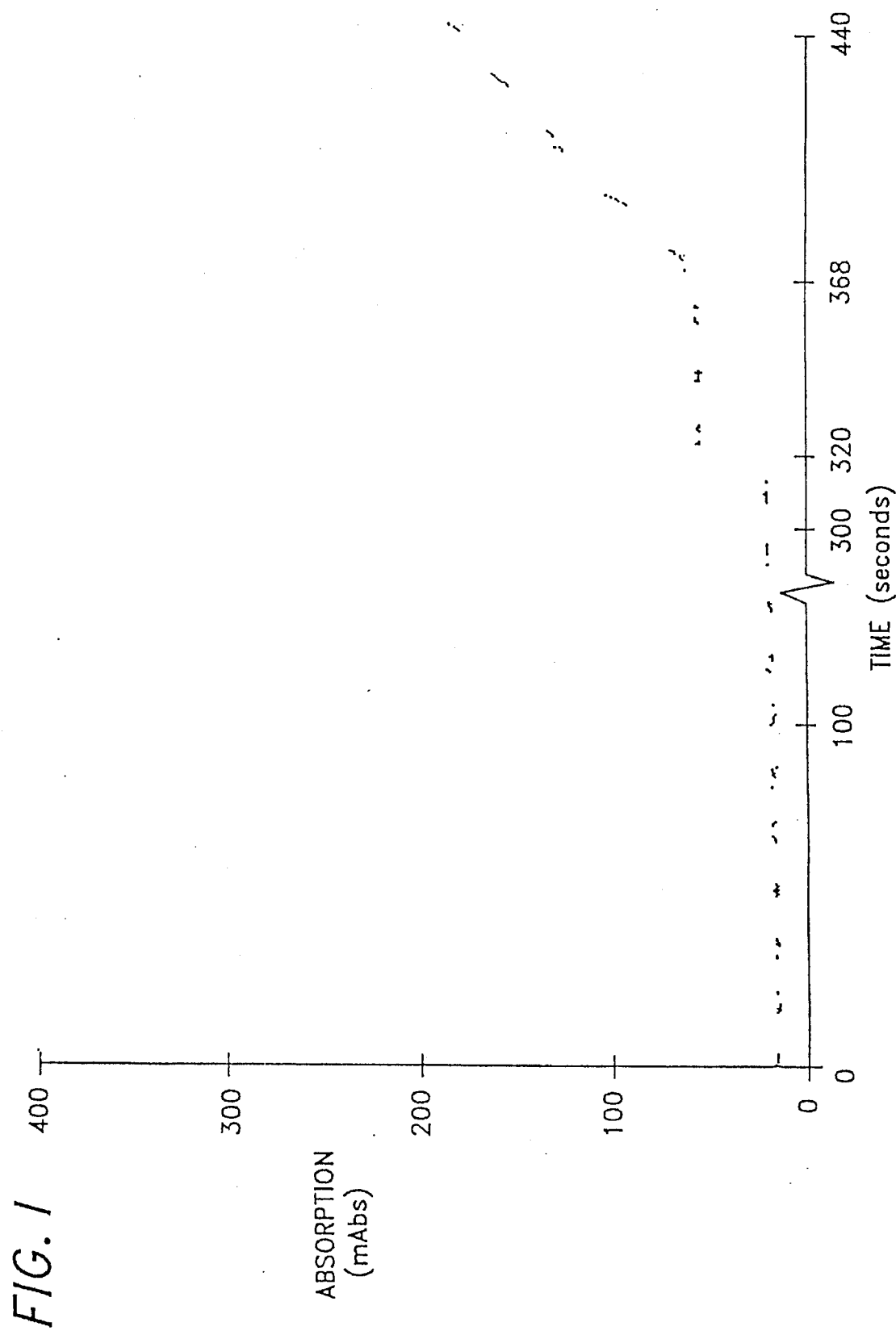

United States Patent [19]

Oh et al.

[11] Patent Number: 5,583,055
[45] Date of Patent: Dec. 10, 1996

[54] INITIAL RATE PHOTOMETRIC METHOD FOR IMMUNOASSAY

[75] Inventors: Chan S. Oh, Diamond Bar; Elizabeth K. Kearns, Chino, both of Calif.

[73] Assignee: Beckman Instruments, Inc., Fullerton, Calif.

[21] Appl. No.: 301,236

[22] Filed: Sep. 6, 1994

Related U.S. Application Data

[62] Division of Ser. No. 916,519, Jul. 17, 1992, Pat. No. 5,371,021.

[51] Int. Cl.$^6$ ............................................. G01N 33/557
[52] U.S. Cl. .................. 436/517; 435/7.1; 436/536; 436/537; 436/34; 436/171
[58] Field of Search ........................ 436/517, 536–539, 436/34, 171, 805; 435/7.1, 962

[56] References Cited

U.S. PATENT DOCUMENTS

| | | | |
|---|---|---|---|
| 4,204,837 | 5/1980 | Sternberg et al. | 436/517 |
| 4,205,954 | 6/1980 | Barson | 356/339 |
| 4,224,304 | 9/1990 | Sawai et al. | 424/12 |
| 4,305,665 | 12/1981 | Achter et al. | 356/339 |
| 4,313,929 | 2/1982 | Morita et al. | 424/12 |
| 4,446,239 | 5/1984 | Tsuji et al. | 436/532 |
| 4,521,521 | 6/1985 | Abbott et al. | 436/517 |
| 4,554,257 | 11/1985 | Aladjem et al. | 436/519 |
| 4,604,365 | 8/1986 | O'Neill et al. | 436/528 |
| 4,647,544 | 3/1987 | Nicoli et al. | 436/518 |
| 4,766,083 | 8/1988 | Miyashita et al. | 436/517 |
| 4,835,110 | 5/1989 | Seymour et al. | 436/517 |
| 5,162,236 | 11/1992 | Pang et al. | 436/517 |
| 5,169,757 | 12/1992 | Yamazaki et al. | 435/7.92 |

FOREIGN PATENT DOCUMENTS

| | | |
|---|---|---|
| 47803/90 | 9/1990 | Australia . |
| 0013306A1 | 7/1980 | European Pat. Off. . |
| 0090966A1 | 10/1983 | European Pat. Off. . |
| 0216177A3 | 4/1987 | European Pat. Off. . |
| 0315317 | 5/1989 | European Pat. Off. . |
| 0368462A1 | 5/1990 | European Pat. Off. . |
| 3615384A1 | 11/1986 | Germany . |
| 55-44903 | 3/1980 | Japan . |
| WO89/00694 | 1/1989 | WIPO . |

OTHER PUBLICATIONS

Foster, R. C. et al., "Turbiometry", Chapter 5 of Manual of Clinical Laboratory Immunology, 3d edition (1986) pp. 25–32.
Sternberg, J. C., "Rate Nephelometry", Chapter 6 of Manual of Clinical Laboratory Immunology, 3d edition (1986) pp. 33–37.
Sternberg, J. C., "A Rate Nephelometer For Measuring Specific Proteins By Immunoprecipitin Reactions", Clin Chem, 23/8, 1456–1464 (1977).
Finley, P. R., et al., "Rate–Nephelometric Inhibition Immunoassay Of Phenytoin And Phenobarbital", Clin. Chem. 27/3, 405–409 (1981).
Killingsworth et al, "Nephllometric Studies of the Precipitin Reaction: A Model System for Specific Protein Measurements," Clin. Chem. 19 (4):403–407, (1973).
Muratsugu et al, "Detection of Antistreplolysin O Antibody: Application of an Initial Rate Method of Latex Prezoelectric Immunoassay, " Anal. Chem. 64(21):2483–2487, (1992).
Savory et al, "Kinetics of the IgG–anti–IgG Reaction, as Evaluated by Conventional and Stopped–Flore Nephelometry," Clin. Chem. 20(8):1071–1075, (1974).

*Primary Examiner*—Carol A. Spiegel
*Attorney, Agent, or Firm*—William H. May; Gary T. Hampson; Sheldon & Mak

[57] ABSTRACT

An initial rate photometric immunoassay method useful for detecting and quantifying analytes in various physiological fluids is disclosed. The method is carried out by combining in a liquid medium an undiluted sample of analyte-containing physiological fluid, such as serum, and an excess of an anti-analyte antibody. A substantially constant initial rate of increase of the liquid medium's turbidity, due to the resulting immunoprecipitation reaction, is measured in real time and compared to a calibration curve prepared from known analyte concentrations to detect and quantify the analyte. Detection and quantification of numerous analytes including, haptens, drugs and proteins, in a wide variety of physiological fluids can be rapidly carried out by the present method.

8 Claims, 7 Drawing Sheets

INITIAL RATE PHOTOMETRIC METHOD FOR IMMUNOASSAY

This is a divisional of application Ser. No. 07/916,519, now U.S. Pat. No. 5,371,021, filed Jul. 17, 1992.

BACKGROUND

We have invented a new photometric immunoassay method for detecting and quantifying various analytes in physiological fluids. Our invention is directed in particular to an initial rate photometric immunoassay method.

There is a continuing need for a rapid, accurate, and reproducible method for the detection and quantification of various naturally synthesized substances, such as antibodies, antigens, and hormones at low concentrations. Additionally, there is an extensive and pervasive need to detect other biologically active substances such as drugs and toxins in physiological fluids. Detection of therapeutic drugs and drugs of abuse can be very important to, for example, medical therapy, law enforcement and employment decisions.

Clinical chemistry laboratory tests are an important part of a health care system. Physicians frequently use such tests to monitor serum protein and therapeutic drug levels where only a narrow safe serum level for a drug may exist. Typically, microgram concentrations of a particular drug in a physiological fluid, such as serum, plasma, urine, amniotic, pleural or cerebrospinal fluid must be determined to permit effective medical treatment or to detect nontherapeutic use of opiates such as heroin, morphine and cocaine. With billions of clinical chemistry tests being performed annually, the speed, accuracy and cost control of such tests are important objectives.

A number of commonly used clinical chemistry tests detect and quantify various substances present in physiological fluids through an immunoprecipitation reaction. An immunoprecipitation reaction can occur when two reaction partners, each with a specific binding affinity for the other, are combined in a suitable liquid medium. The reaction partners can be an antigen and a specific binding partner for the antigen, such as an antibody. Generally, one of the reaction partners is present in an unknown amount in a sample of the physiological fluid, and is called the analyte. Typically, the liquid medium is a buffered aqueous solution. Once initiated, the immunoprecipitation reaction results in the formation of immunoprecipitates, or antibody-antigen complexes that are usually insoluble, but which can also be soluble, in the liquid medium.

The presence of immunoprecipitates in the liquid medium can change optical properties, such as light scattering and light absorption properties of the liquid medium, by attenuation of incident light energy. These changes can be detected by an appropriate photometer. The photometer can be calibrated to permit detection and quantification of an analyte. Calibration is typically carried out by conducting the immunoprecipitation reaction with known amounts of an analyte of interest, to derive a standard or calibration curve. The calibration curve can show a level of light attenuation, for example light absorption, by the liquid medium versus amount of analyte present per unit volume of a physiological fluid.

Photometric immunoassay techniques include nephelometry and turbidimetry. In nephelometric immunoassay, a photometer is used to measure the reflection or scatter of light by immunoprecipitates towards a light detector. The immunoprecipitates can be aggregates of an analyte and a specific binding partner for the analyte, or aggregates of an analyte-conjugate and the specific binding partner. The amount of light scattered by the immunoprecipitates is directly proportional to the number of immunoprecipitates present, which typically increases as the immunoprecipitation reaction proceeds. This proportionality permits a quantitative determination of analyte concentration. In turbidimetric immunoassay, an attenuation or reduction of light energy passing through a liquid medium containing immunoprecipitates is measured by a light detector placed in the light path. The light energy reduction can be caused by reflection, scatter, and absorption of the incident light by the immunoprecipitates. The amount of light reduction caused by the immunoprecipitates is, again, directly proportional to the number of immunoprecipitates present, permitting a quantitative determination of analyte concentration.

In either nephelometric or turbidimetric immunoassay, the photometer can be used to measure the extent of change of an optical property of the liquid medium after the immunoprecipitation reaction has essentially run to completion (i.e. an end point determination). Alternately, the photometer can be used to detect the rate of change of an optical property of the liquid medium at a particular time after commencement of the immunoprecipitation reaction (i.e. a rate determination). Immunoassay by known end-point or known rate photometric methods presents problems and inefficiencies, particularly where an objective is to detect and quantify drug and protein levels in a large number of physiological fluid samples in the shortest possible time.

With regard to photometric end point immunoassays, these problems include the inherent slowness of end point methods. Thus, with end point methods, the immunoprecipitation reaction is allowed to go to or near reaction completion, before a photometric reading of light scatter or increased liquid medium turbidity is made. Hence, analyte detection is delayed until at least about five minutes or more after the immunoprecipitation reaction has begun. Additionally, the throughput or analysis rate per unit of time where multiple samples are to be analyzed is low. Such delays force concomitant delays in diagnostic and therapeutic decision-making.

Additionally, photometric end point immunoassay methods generally require at least some sample manipulation prior to analysis. Typically, dilution of an analyte-containing physiological fluid sample is carried out by, for example, adding an aliquot of the physiological fluid to saline. A dilution step is required because besides analyte, the physiological fluid usually also contains many other substances such as proteins, steroids, hormones, drugs and a variety of metabolites, that can cause nonspecific immunoprecipitation reactions or otherwise affect optical properties of the liquid medium. Thus, a very high level of interfering or background light scatter and light absorbance occurs when an aliquot from an neat (i.e. undiluted) sample of analyte-containing physiological fluid is used. Hence, end point determination of analyte with an undiluted physiological fluid sample is very difficult or impossible.

Any sample manipulation, including sample dilution, is undesirable because it delays sample analysis and inherently carries the risk of the sample becoming contaminated or of otherwise interfering with an accurate analyte detection and quantification. Furthermore, sample manipulation, by increasing worker human contact time with the sample, increases the risk of disease transmission from sample to the sample handler.

Photometric rate immunoassay methods also have deficiencies. Maximum rate nephelometry and peak rate turbidimetry detect analytes by measuring the maximum rate of a changing optical characteristic of the liquid medium in which the immunoprecipitation reaction takes place. A first deficiency exists because in these known methods, the photometrically detected maximum or peak rate typically does not occur until at least about a minute or more after the beginning of the photometrically detectable immunoprecipitation reaction. Hence, as with end point immunoassay methods, the known rate methods are slow and prevent achievement of a high sample throughput per unit time.

A second problem with photometric rate immunoassay methods is due to the nature of the rate signals detected. The existing rate immunoassay methods typically do not detect a substantially constant or linear-with-time photometric rate signal. A nonlinear-with-time rate signal can require use of time consuming and complicated mathematical formulae to fit the nonlinear rate curve derived from the signal to a linear approximation. Rapid analyte detection and high sample throughput are thereby hindered.

A third problem with known photometric rate immunoassay methods arises from the variability of the time at which the peak or maximum rate signal occurs. Depending on factors such as analyte concentration, specific binding partner concentration, and nature of the analyte and the specific binding partner, the maximum or peak rate signal can occur at widely varying times after initiation of a photometrically detectable immunoprecipitation reaction. Thus, when dealing with one or more unknowns, such as analyte concentration, it can not be determined beforehand when the analytically useful maximum or peak rate signal will occur. Hence, the photometer used is either set to detect signal at a particular time or times, in hopes of catching the right signal, or the immunoprecipitation reaction is tracked continuously until the desired signal occurs. This uncertainty regarding when the maximum or peak rate signal will occur leads to loss of time, inefficiency in analysis, and additional expense.

Thus, there is a need for a photometric immunoassay method that permits: (1) rapid analyte detection; (2) analyte detection in both undiluted (neat) and diluted samples; (3) accurate analyte quantification; (4) high sample throughput per unit time; and (5) low per-sample analyzed cost.

SUMMARY

The present invention meets these needs. Our invention permits rapid detection and quantification of a wide variety of analytes in both undiluted and diluted samples, with high accuracy, high sample throughput per unit time, and at a low per-sample analyzed cost. These objectives are accomplished by the disclosed methods for initiating and detecting a photometrically detectable immunoprecipitation reaction in a liquid medium. The disclosed methods permit initiation of immunoprecipitation reactions that produce reaction rate signals that are analytically useful, substantially constant, detectable at a substantially constant time after initiation of the reaction, and that are detectable within less than about one minute after initiation of the reaction.

Definitions

The following definitions of various terms used in this application are provided to facilitate understanding the present invention.

"About" when used to qualify a specific numerical value, such as for example a unit of time, means that the numerical value can be as much as twenty percent greater than or as much as twenty percent less than the stated numerical value.

"Analyte" means the substance or group of substances to be detected and/or quantified in a physiological fluid. The term "analyte" encompasses analyte analogs.

"Analyte analog" means a substance that can specifically bind to a reaction partner for the analyte in much the same manner as the analyte itself.

"Bidentate" or "bidentate conjugate" means a heterobifunctional conjugate with two chemical moieties, or bidentate members, attached by a spacer moiety, with each member being capable of specifically binding to a different macromolecule. Further definition and details regarding bidentate conjugates can be found in U.S. Pat. No. 5,196,351.

"Conjugate" means a compound to which an analyte can be or is bound to, thereby enabling the analyte to participate in a photometrically detectable immunoprecipitation reaction.

"Hapten" means a partial or incomplete antigen, typically a low molecular weight drug, that is generally incapable of causing by itself a significant production of antibodies.

"Initial rate" means a photometrically detectable, substantially constant rate of change of a photometric property of a liquid medium that can be detected within about one minute after initiation of a photometrically detectable immunoprecipitation reaction in the liquid medium.

"Nephelometry" means a photometric method for detecting and quantifying an analyte by measurement of the light scatter by immunoprecipitates. The immunoprecipitates can be aggregates of analyte and specific binding partner and/or of analyte-conjugate and the specific binding partner. The photometer used has a light source and a light detector that are not aligned substantially opposite each other, that is not along the same axis.

"Photometric method" means a method that uses a photometer capable of generating and detecting ultra violet, visible or infrared light to detect the initial rate of an immunoprecipitation reaction.

"Turbidimetry" means a photometric method for detecting and quantifying an analyte by measurement of a light attenuation due to immunoprecipitates. The immunoprecipitates can be aggregates of analyte and specific binding partner and/or of analyte-conjugate and the specific binding partner. The photometer used has a light source and a light detector that are aligned substantially opposite each other, that is along the same axis.

An initial rate photometric method according to the present invention can be used to rapidly and accurately detect and quantify numerous different analytes in a wide variety of physiological fluids. The physiological fluid used can be diluted, or preferably undiluted. The present method permits high sample throughput, and a low per-sample analyzed cost.

Unlike known photometric immunoassays, the present method can detect and quantify analytes by detecting the initial rate of change of a photometric property of a liquid medium in which an immunoprecipitation reaction is occurring.

A preferred embodiment of the initial rate method proceeds by combining in a liquid medium, an analyte-containing sample, and a specific binding partner for the analyte. An analyte-protein conjugate can also be added to the liquid medium. Both the analyte and the analyte-conjugate are capable of binding to the specific binding partner. A photometrically detectable immunoprecipitation reaction is thereby initiated in the liquid medium. The specific binding partner for the analyte can be either a polyclonal or a monoclonal antibody.

The immunoprecipitation reaction is detectable because immunoprecipitates are formed during the reaction. The immunoprecipitates can be complexes of the analyte and the specific binding partner and/or of an analyte-conjugate and the specific binding partner.

The analyte is detected by detection of a substantially constant or linear-with-time initial rate of change of a photometric property of the liquid medium. Preferably, detection of this initial rate is commenced within a period of time that begins with initiation of the photometrically detectable immunoprecipitation reaction and that ends about 60 seconds after the beginning of the reaction. Preferably, detection of the initial rate is terminated within a period of time that begins with the reaction and ends about 5 minutes after the beginning of the reaction.

In additional preferred embodiments of the invention, detection of the substantially constant initial rate of change of the photometric property of the liquid medium commences within a period of time that begins with the photometrically detectable immunoprecipitation reaction and ends about forty, thirty, or twenty seconds after the beginning of the reaction. In a particularly preferred embodiment of the invention, detection of the substantially constant initial rate commences within a period of time that begins with the reaction and ends about ten seconds after the reaction begins.

In further preferred embodiments of the present invention, detection of the substantially constant initial rate terminates within a period of time that begins with the reaction and ends about four minutes, three minutes, two minutes, sixty seconds, fifty seconds, forty seconds, or thirty seconds after the beginning of the reaction. In a further particularly preferred embodiment of the present invention, detection of the substantially constant initial rate terminates within a period of time that begins with the reaction and ends about twenty seconds after the beginning of the reaction.

The initial rate of change of the photometric property of the liquid medium is preferably compared to a standard or calibration curve derived by carrying out the same immunoprecipitation reaction with known amounts of analyte. In this manner, the concentration of an unknown analyte per unit volume of a physiological fluid can be determined. Thus, photometric detection of the initial rate of a photometrically detectable immunoprecipitation reaction by the present method permits very rapid analyte detection and quantification, and a high sample throughput per unit time.

Where the analyte is a hapten, unable by itself to engage in a photometrically detectable immunoprecipitation reaction, a competitive inhibition immunoprecipitation reaction between the hapten-analyte and a hapten-analyte conjugate is initiated. The analyte and the analyte-conjugate compete for binding sites on the same specific binding partner. The reaction of the larger analyte-conjugate with the specific binding partner results in the photometrically detectable immunoprecipitation reaction. The rate of this detectable reaction is inversely proportional to the amount of the hapten analyte present. Hence, detection and quantification of an analyte present in an unknown concentration can be accomplished.

Preferably, the specific binding partner and the analyte are combined in the liquid medium in a molar ratio of at least about 1.2 specific binding partner to about 1.0 analyte (i.e. 1.2:1). The ratio of the specific binding partner to the analyte-conjugate is preferably greater than about 1:1 and less than or equal to about 10:1. More preferably, the ratio of the specific binding partner to the analyte-conjugate is at least about 1.2:1 and less than or equal to about 10:1.

To help control the rate of the photometrically detectable immunoprecipitation reaction, the liquid medium preferably contains one or more additives. A suitable additive can be a dextran, a glycol or a derivative thereof.

Another preferred embodiment of the initial rate method has the steps of firstly combining, in a liquid medium, an undiluted sample of an analyte-containing physiological fluid, and a specific binding partner for the analyte. The second step is to initiate a photometrically detectable immunoprecipitation reaction in the liquid medium. The third step is to irradiate the liquid medium with light. Irradiating the liquid medium with light produces a photometrically detectable initial rate signal. The signal can be a light attenuation signal, for example, a light scatter or a light absorption signal. The fourth step is to detect the analyte by commencing detection and by terminating detection of the substantially constant initial rate of change of a photometric property of the liquid medium within a period of time that begins with initiation of the photometrically detectable immunoprecipitation reaction and which period of time ends about 60 seconds after the beginning of the reaction. The fifth and final step is to quantify the amount of analyte present per unit volume of the physiological fluid.

Preferably, when added to the liquid medium, the analyte is present in an undiluted sample of a physiological fluid, such as serum, thereby expediting analyte detection and a high sample throughput. Additionally, using an undiluted sample reduces a technician's contact time with the sample, thereby helping to prevent both potential sample contamination and disease transmission from the sample.

An additional preferred and more detailed embodiment of the present initial rate method uses a photometer that has at least a light source and a light detector, and which embodiment has the following steps: arranging the light detector in front of the light source, so that the light source and the light detector are aligned along substantially the same axis; interposing a substantially optically transparent container between the light detector and the light source; combining in the liquid medium in the container, a sample of an undiluted physiological fluid containing analyte, and an excess of an anti-analyte antibody; initiating a photometrically detectable immunoprecipitation reaction in the liquid medium; irradiating the liquid medium in the container with light of a suitable wavelength from the light source; detecting the substantially constant rate of increasing turbidity of the liquid medium with the light detector at a first time within about 20 seconds after initiation of the photometrically detectable immunoprecipitation reaction in the liquid medium; repeating the irradiating step and the detecting step at a second later time less than about 60 seconds after initiation of the reaction; measuring the change in the turbidity of the liquid medium from the first time to the second later time, thereby deriving an initial rate of change of turbidity of the liquid medium; detecting the analyte; and quantifying the amount of the analyte present per unit volume of the physiological fluid from the change in the initial rate of liquid medium turbidity from the first time to the second later time.

Analytes detectable and quantifiable by the present initial rate method include drugs (both therapeutic drugs and drugs of abuse), toxins, antigens, peptide hormones, steroids, vitamins, proteins, and metabolites and derivatives thereof.

DRAWINGS

These and other features, aspects, and advantages of the present invention can become better understood from the following description, claims and the accompanying drawings where:

FIG. 1 graphically shows a substantially constant rate of increasing light attenuation by a liquid medium wherein gentamicin, a gentamicin conjugate, and an antigentamicin antibody were combined to initiate a photometrically detectable immunoprecipitation reaction.

Figure 2:
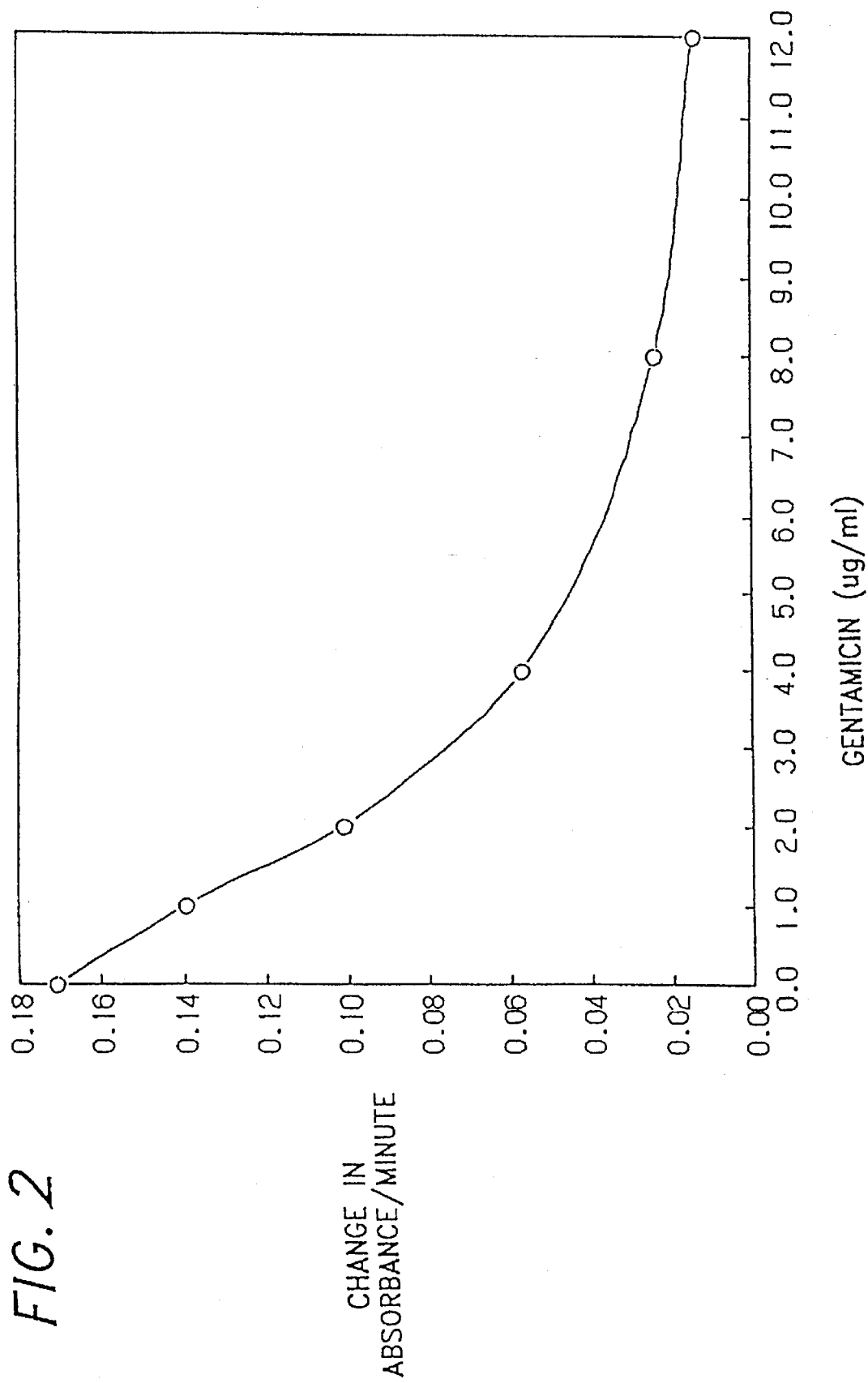

FIG. 2 graphically shows a standard curve of the rate of increasing light attenuation by a liquid medium wherein known amounts of gentamicin, a gentamicin conjugate, and an anti-gentamicin antibody were combined to initiate a photometrically detectable immunoprecipitation reaction.

Figure 3:
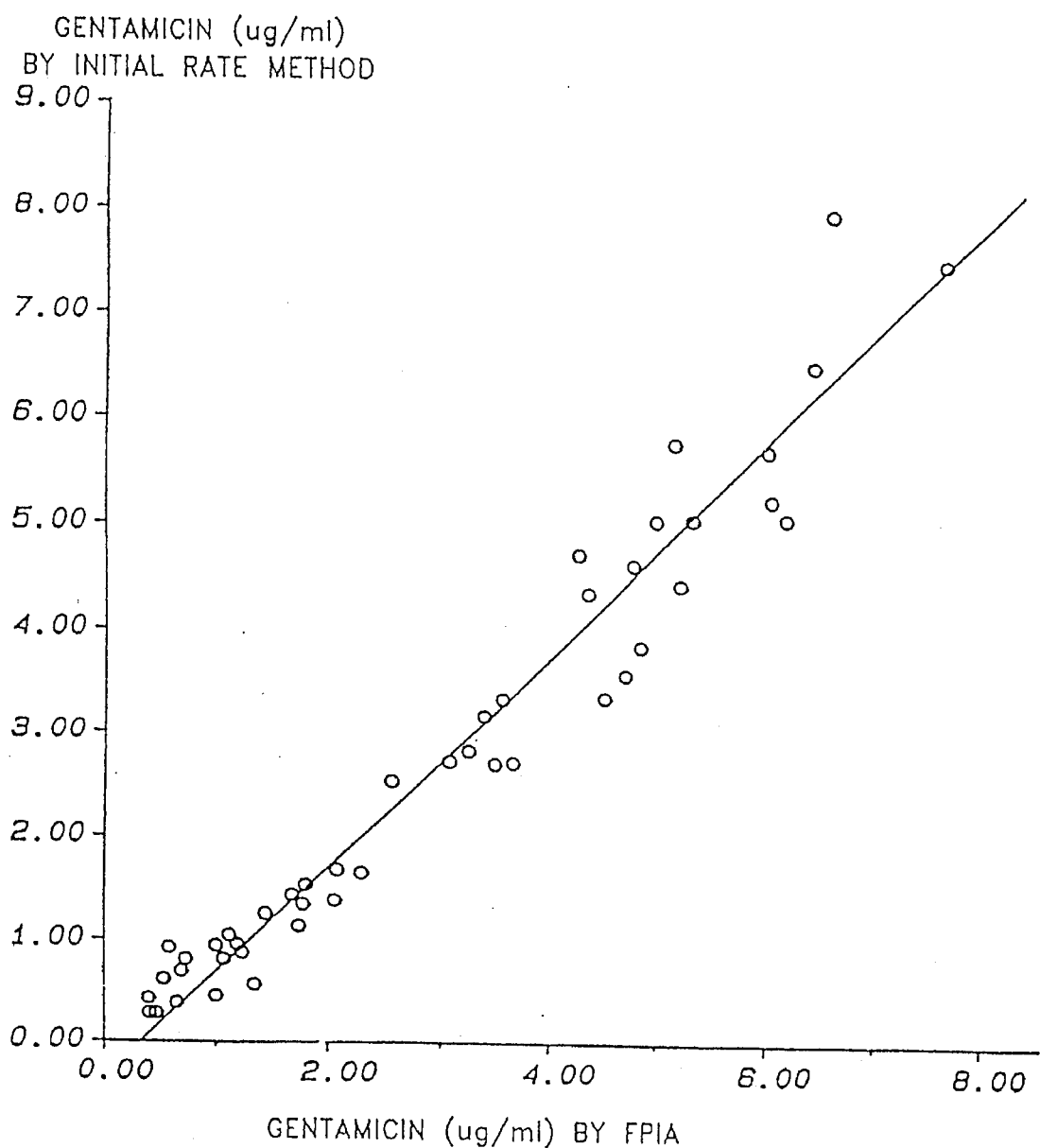

FIG. 3 graphically shows a correlation of the gentamicin concentrations detected in 46 samples by the present initial rate method on the vertical axis, with the gentamicin concentrations detected in the same 46 samples by fluorescent polarization immunoassay (FPIA) on the horizontal axis. The relationship between values on the vertical axis (y) and those on the horizontal axis (x) is described by the function: y=1.0139×0.3286.

Figure 4:
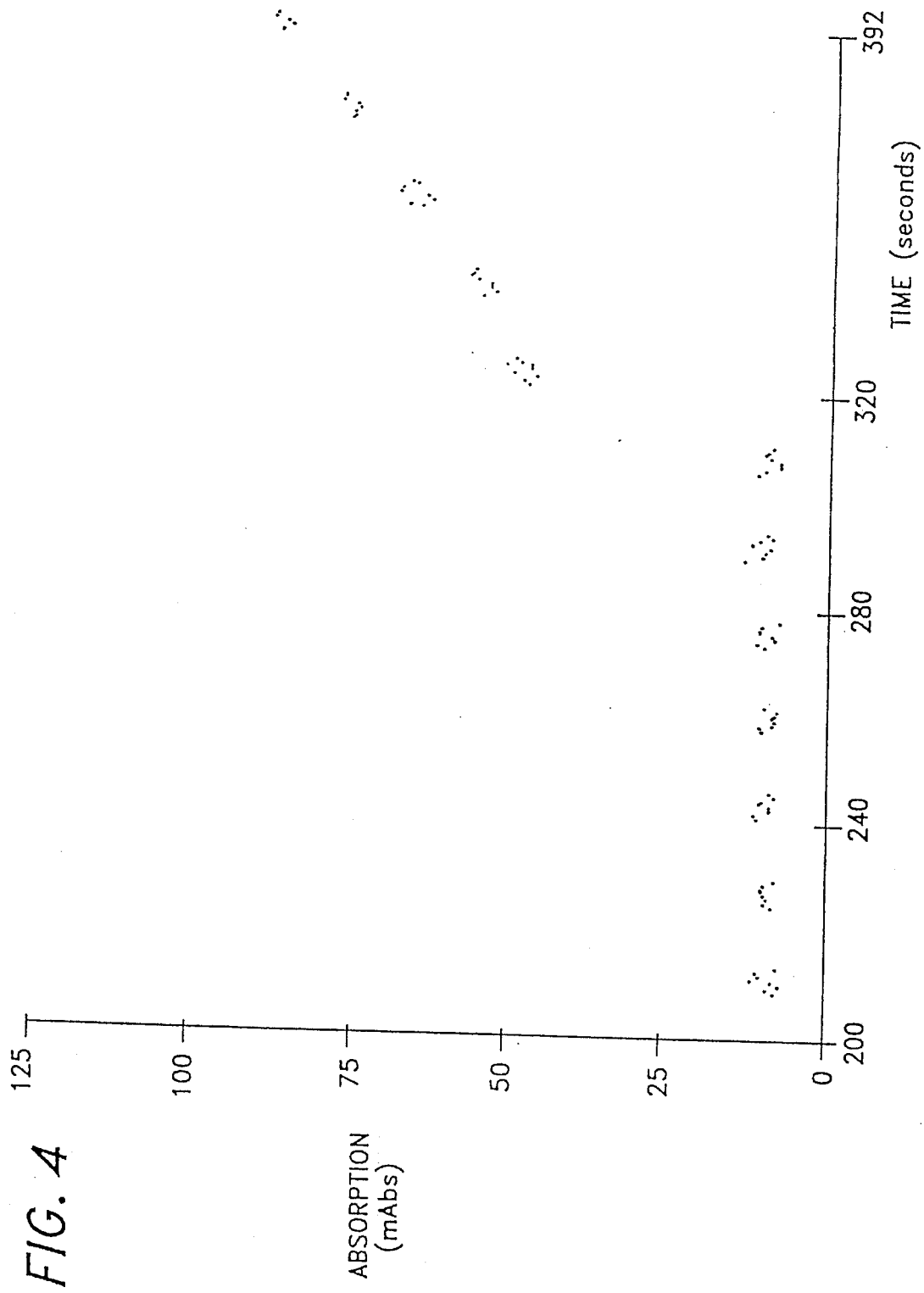

FIG. 4 graphically shows a substantially constant rate of increasing light attenuation by a liquid medium wherein IgM, and an anti-IgM antibody were combined to initiate a photometrically detectable immunoprecipitation reaction.

Figure 5:
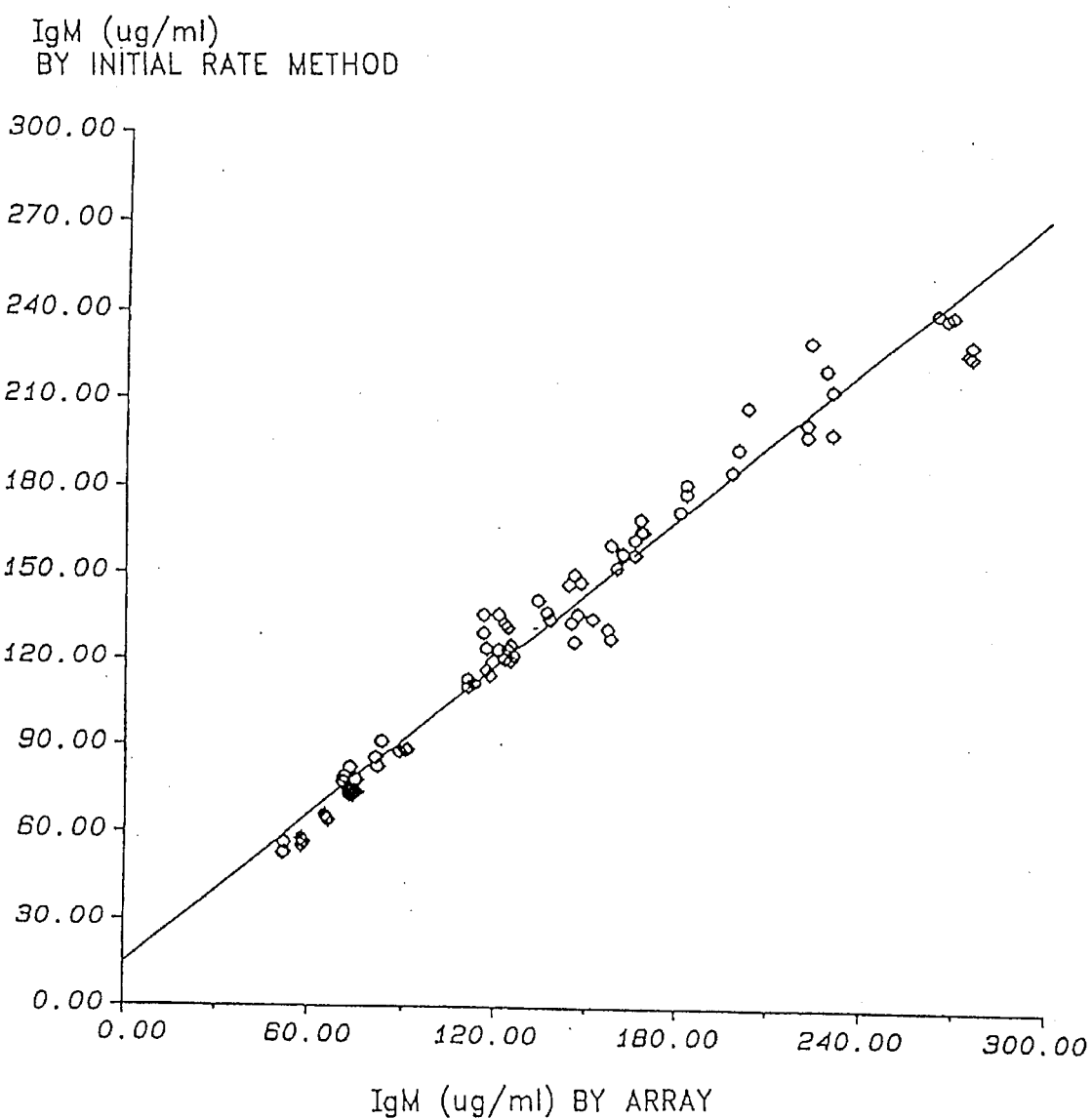

FIG. 5 graphically shows a correlation of the IgM concentrations detected in 83 samples by the present method on the vertical axis, with the IgM concentrations detected in the same 83 samples by Array® nephelometry on the horizontal axis. The relationship between values on the vertical axis (y) and those on the horizontal axis (x) is described by the function: y=0.8907×11.6158.

Figure 6:
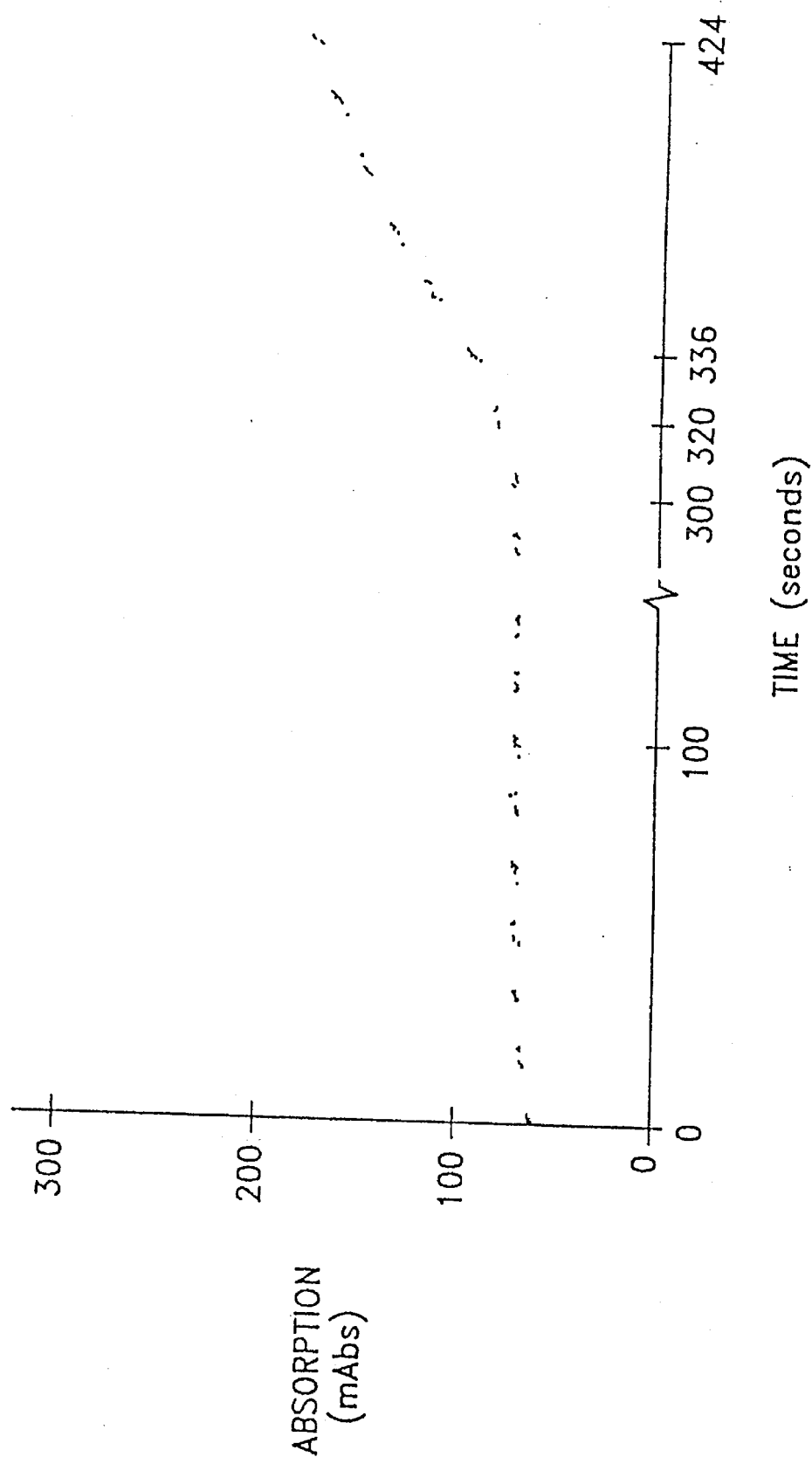

FIG. 6 graphically shows a substantially constant rate of increasing light attenuation by a liquid medium wherein valproic acid, a valproic acid conjugate, and an anti-valproic antibody were combined to initiate a photometrically detectable immunoprecipitation reaction.

Figure 7:
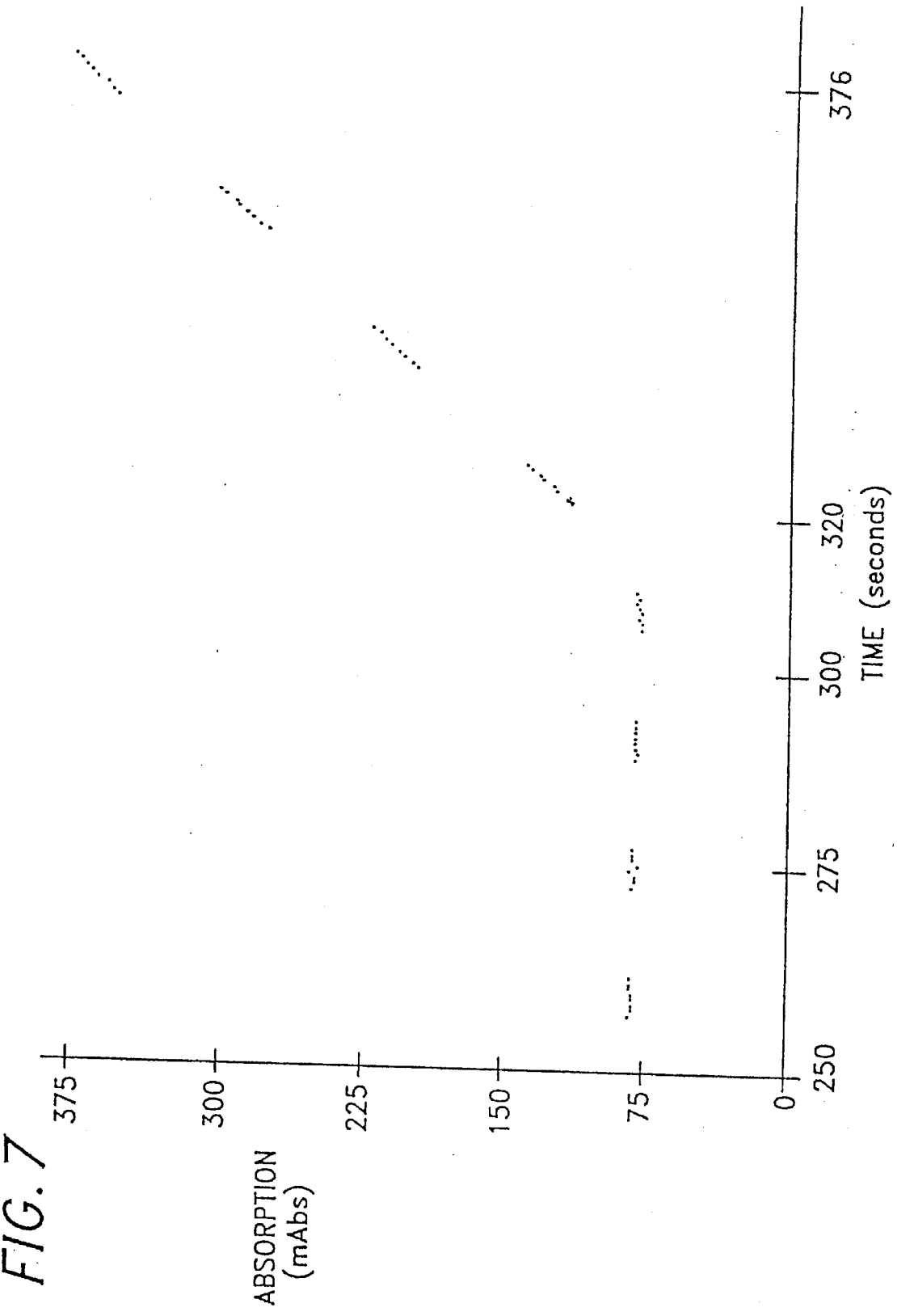

FIG. 7 graphically shows a substantially constant rate of increasing light attenuation by a liquid medium wherein haptoglobin, and an anti-haptoglobin antibody were combined to initiate a photometrically detectable immunoprecipitation reaction.

DESCRIPTION

Our invention is based upon the discovery that the initial rate of change of a photometric property of a liquid medium, upon initiating a photometrically detectable immunoprecipitation reaction in the liquid medium, can be used to detect and quantify an analyte. We have applied this discovery to develop an initial rate photometric immunoassay method by which a wide diversity of analytes present in various physiological fluids can be rapidly detected and quantified.

Photometric detection is carried out by detecting an attenuation of light energy passing through the liquid medium. The light energy attenuation is due to scattering and/or absorption of the light by immunoprecipitates in the liquid medium.

We discovered that by practicing the disclosed method, a photometric rate signal that is substantially linear-with-time for an initial period of an ongoing immunoprecipitation reaction can be detected. Hence, photometric detection of the immunoprecipitation reaction yields a substantially constant rate signal of increasing liquid medium light attenuation. The substantially constant initial rate of the signal detected can be maintained for a period of about 5 minutes or more after initiation of the reaction.

By "substantially constant" or "substantially linear-with-time" it is meant that upon performing a regression analysis, such as a least square fit regression analysis, to the initial rate signal data obtained from initiating a photometrically detectable immunoprecipitation reaction in a liquid medium, and plotted as light attenuation versus time (i.e. for FIGS. 1, 4, 6, and 7, the initial rate signal data plotted commencing at time zero plus 368 seconds, time zero plus 320 seconds, time zero plus 336 seconds, and time zero plus 320 seconds respectively), the initial rate signal data exhibits, in relation to the regression line obtained, a correlation coefficient r that is greater than or equal to about 0.75. Preferably, the correlation coefficient r is greater than or equal to about 0.90, so that the initial rate signal detected is essentially constant.

The substantially constant rate of the light attenuation signal detected can be maintained for about 5 minutes or more by providing sufficient specific binding partner for participation in an immunoprecipitation reaction of such length. An additional factor important for maintaining the substantially constant initial rate reaction for such a period of time is provision of sufficient reaction partner in the liquid medium for the specific binding partner.

Additionally, the substantially constant rate signal can be detected at the same time, typically almost immediately upon commencement of the photometrically detectable immunoprecipitation reaction, irrespective of the nature of the particular analyte being assayed.

Furthermore, we have determined that the substantially constant initial rate of the photometrically detectable immunoprecipitation reaction is also the maximum rate of the reaction. These characteristics of our invention permit accurate and rapid analyte detection and quantification.

The present method can be used to detect and quantify any analyte for which a specific binding partner, such as an antibody, exists or can be developed. Such analytes include drugs, toxins, vitamins, antibodies, pesticides, steroids, peptide hormones, proteins, and various metabolites and derivatives thereof. Analytes of particular interest include drugs (both therapeutic drugs and drugs of abuse) and proteins with low concentrations in biological fluids or with narrow therapeutic ranges.

The method proceeds by combining in the liquid medium an analyte-containing sample, and a specific binding partner for the analyte. This first step can initiate a photometrically detectable immunoprecipitation reaction in the liquid medium, if the resulting analyte-specific binding partner aggregates form photometrically detectable complexes in the liquid medium.

The next step in the method is to commence detection of the substantially constant initial rate of change of a photometric property of the liquid medium. Detection of the initial rate is terminated after a sufficient detection time has elapsed to permit analyte detection. Typically, less than about 60 seconds of total detection or signal reading time is required for analyte detection and quantification. Preferably, total signal detection time is between about 5 seconds and about 40 seconds to expedite sample analysis, while still permitting accurate analyte detection and quantification. More preferably, total signal detection time is between about 8 seconds and about 24 seconds to further expedite sample analysis, without sacrificing accurate analyte detection and quantification. In a particularity preferred embodiment of the present invention total signal detection time is between about 8 seconds and about 16 seconds.

Detection of the substantially linear-with-time initial rate signal preferably commences within about the first minute after initiation of the photometrically detectable immunoprecipitation reaction, to expedite sample analysis. The initial rate method can be advantageously practiced by commencing detection within about the first 40, 20, or even within about the first 10 seconds after initiation of the photometrically detectable immunoprecipitation reaction.

Termination of detection of the substantially linear-with-time initial rate signal preferably occurs within about five minutes after initiation of the photometrically detectable immunoprecipitation reaction, to again expedite sample analysis. The initial rate method can be advantageously practiced by terminating detection of the initial rate signal within about 4, 3, 2, or 1 minute after initiation of the photometrically detectable immunoprecipitation reaction. We have found that the accuracy of the analyte detection and quantification results obtained are not sacrificed by terminating detection of the initial rate signal within about 50, 40, 30, or even 20 seconds after initiation of the photometrically detectable immunoprecipitation reaction.

Photometric detection is carried out using a photometer that has at least a light source and a light detector. The liquid medium is held by a substantially optically transparent container and the container is placed in the path of the incident light from the light source. The light detector detects a change to an optical or photometric property of the liquid medium as the immunoprecipitation reaction proceeds.

A factor relevant to obtaining the desired substantially constant initial rate signal, is the presence of an excess of specific binding partner to the amount of analyte, or analyte-conjugate, present in the liquid medium. Hence, a ratio of specific binding partner to analyte, or to analyte-conjugate, of about 1:1 or less is typically not preferred. An excess of specific binding partner facilitates obtaining the desired substantially constant and maximum rate of the immunoprecipitation reaction. Generally, relatively small volumes of analyte-containing sample are used in relation to the volumes of specific binding partner solution combined in the liquid medium, to facilitate obtaining the desired stoichiometric excess of specific binding partner over analyte.

Preferably, the ratio of binding partner to analyte, or to analyte-conjugate, is at least about 1.2:1, to provide sufficient binding partner to achieve the desired photometrically detectable initial rate signal from the immunoprecipitation reaction. More preferably, the ratio of binding partner to analyte-conjugate is between about 1.2:1 and about 10:1, to provide sufficient specific binding partner to sustain the substantially constant initial rate signal during the signal detection period. When the ratio of specific binding partner to analyte-conjugate is greater than about 10:1 problems such as non-specific precipitation and rate signal interference can occur and prevent an accurate analyte detection and quantification. Where an analyte-conjugate is not used, as for most protein immunoassays by the present initial rate method, the specific binding partner to analyte ratio can be as high as about $10^6$:1 before the amount of binding partner becomes so excessive as to again cause problems such as non-specific precipitation and rate signal interference.

Other factors which can affect obtaining the desired initial linear photometric rate signal include analyte-conjugate, and analyte concentrations in the liquid medium.

Analytes detected and quantified by the present method include numerous drugs, some of which are haptens. Haptens are generally too small to cause a detectable liquid medium photometric property change upon being combined with a specific binding partner in the liquid medium. Hence, for such an analyte it is necessary to conjugate the hapten drug (or a metabolite of the hapten drug) to a larger molecule, such as a carrier protein to thereby obtain an analyte-conjugate. The analyte-conjugate is then used in a competitive inhibition immunoassay version of the initial rate method.

The conjugate used can be any substance capable of binding to the hapten drug to produce a drug conjugate that can then participate in a photometrically detectable immunoprecipitation reaction with an anti-drug antibody. Thus, apoferritin or latex particles conjugated to the drug can be used. A preferred conjugate is a protein carrier because of their ready availability and reaction stability. A more preferred conjugate is made by complexing avidin to a biotinylated derivative of the drug to be assayed. Biotin-avidin conjugates can enable a wide variety of hapten-analytes to participate in a photometrically detectable immunoprecipitation reactions. A most preferred conjugate is a bidentate conjugate. Details regarding preparation and use of suitable bidentate conjugates can be found in the U.S. Pat. No. 5,196,351 entitled "Novel Bidentate Conjugate and Method of Use Thereof" serial number and which patent is incorporated herein in its entirety by reference.

During an immunoinhibition reaction, the hapten drug conjugate competes with free drug (or drug metabolite) for binding sites on the specific binding partner. The resulting drug-conjugate-specific binding partner complex can cause a photometric property change, such as increased turbidity, of the liquid medium. The presence of free analyte (i.e. the hapten drug) impedes formation complexes and hence impedes the increase of liquid medium turbidity. Thus, the rate of the turbidimetric response signal detected is inversely proportional to the concentration of free hapten drug in the sample.

The initial reaction rate can be detected by any photometric method for measuring light attenuation, such as turbidimetry. Turbidimetry is the preferred photometric method for detecting changing optical properties of the liquid medium wherein an immunoprecipitation reaction is occurring, because the initial rate signal is most substantially linear when turbidimetric signal detection is used.

Preferably, with respect to physiological fluids (and in particular serum), the light attenuation signal is measured at a wavelength of about 340 nm. Below about 340 nm, for example at 280 nm, interference or background signal from protein absorption can occur. Thus, a measuring wavelength below about 340 nm is not preferred. Above about 340 nm, as the absorption wavelength is lengthened, protein signal interference decreases, but significant additional absorptive interference (e.g. from bilirubin) can occur. Hence, an absorption wavelength of about 340 nm is preferred.

One or more additives to the liquid medium can be used to help control or optimize the initial rate photometric signal detected during the immunoprecipitation reaction. The additive is preferably a dextran or a glycol compound, such as a polyethylene glycol (PEG). Conveniently, the additive can be present in a buffer that forms part of the liquid medium. The buffer is combined with a diluent to prepare a running buffer prior to initiation of the immunoprecipitation reaction. The running buffer can be the liquid medium in which a photometrically detectable immunoprecipitation reaction is initiated. The diluent component of the running buffer acts to dilute the specific binding partner and any analyte-conjugate that may be used.

Particular ratios of additive-containing buffer volume to diluent volume have been found to have utility. Thus, a higher ratio of buffer to diluent in the running buffer, and thereby a higher concentration of buffer additive in the liquid medium, results in a faster rate of the immunoprecipitation reaction as evidenced by a faster rate of increasing liquid medium turbidity. The converse is also true.

A higher concentration of rate-controlling additive is used when a given antibody causes a weak photometric rate signal, as it combines with analyte or analyte-conjugate during an immunoprecipitation reaction, to boost the strength of the signal. Thus, where a weak photometrically detectable immunoprecipitation reaction signal is anticipated, higher ratios of additive-containing buffer to diluent are used to make up the running buffer. The concentration of a rate-controlling additive in the liquid medium is not raised to a level at which non-specific precipitation occurs. Preferred buffer volume to diluent volume ratios in the running buffer are between about 0.5:1 and about 8:1 for the particular buffer and diluent reagents specified in the Examples below. When PEG is used as the rate-controlling additive, it is preferably used in the liquid medium in a concentration of from about 4% w/v to about 10% w/v. Below about 4% w/v insufficient PEG is present to boost weak rate signals. Above about 10%-w/v, considerable nonspecific precipitation can occur.

Varying the concentration of the rate-controlling additive in the liquid medium does not significantly affect the substantially linear nature of the initial rate signal of increasing liquid medium turbidity detected during a photometrically detectable immunoprecipitation reaction.

The specific binding partner can consist of or be present in, for example, whole antiserum, a purified antibody, a monoclonal antibody, or a polyclonal antibody. The specific binding partner can also be a mixture or cocktail of two or more different polyclonal or monoclonal antibodies.

Antibodies can be prepared by immunizing a mammal with an antigen, such as an analyte of interest. The polyclonal antibodies resulting from the immunization can be used as reaction partners for the analyte. Alternately, the immunized mammal can be further processed, in conjunction with well known procedures, to derive monoclonal antibodies to the analyte. Typically, this requires removal of the immunized mammal's spleen, fusion of the spleen cells with myeloma cells to produce hybridomas, and cloning of suitable monoclonal antibody producing hybridomas.

The initial rate method has been used to detect and quantify serum concentrations of various analytes, such as gentamicin and tobramycin, to levels as low as about 0.1 μg per ml of serum.

The initial rate of photometric change of a liquid medium is typically difficult to detect with a manually operated photometer. The present invention is, therefore most preferably practiced using an automated, high-speed photometer, suitably calibrated. Calibration can be carried out by firstly initiating an immunoprecipitation reaction in a liquid medium between a sample containing a known concentration of the analyte and a specific binding partner for the analyte. Next, the initial rate of change of the photometric property of the liquid medium caused by the immunoprecipitation reaction is detected by the photometer. These two steps are then repeated with at least one more sample containing a different known concentration of the analyte. This procedure allows establishment of a standard curve of rate of change of the photometric property versus analyte concentration, which curve is used to calibrate the photometer.

An exemplary photometer for practicing the initial rate method is a Beckman Synchron CX® automated random-access analyzer The Synchron CX® clinical analyzer is an high speed automated, computerized work station that can use various photometric protocols to assist rapid detection of different analytes. This instrument can detect a variety of photometric changes to liquid media, including turbidimetric liquid media changes.

The Synchron CX® automated analyzer utilizes a cartridge with three compartments A, B, and C. Each compartment can be loaded with a different fluid, and the cartridge is then inserted into the instrument. Automatic pipettes operated by the instrument aspirate and combine fluid from the three compartments in predefined order and amounts into a substantially optically transparent cuvette. Thereafter, to the combined fluids in the cuvette, the instrument can add an aliquot of a physiological fluid (e.g. undiluted patient serum), followed by photometric detection of the resulting immunoprecipitation reaction.

EXAMPLES

The following examples set forth illustrations of various features and embodiments of the invention and are not intended to limit the scope of the claimed invention.

Example 1

Preparation of Monoclonal Antibodies to Gentamicin

Hybridomas capable of making monoclonal antibody to two forms or species of gentamicin were prepared. The materials used were as follows. The myeloma cells used were derived from the P3X63-Ag8,653 myeloma line, a nonsecreting mouse myeloma line developed by Kearney et al., *J. Immunol.*, 123:1548 (1979). The spleen cells used were taken from Balb/c mice immunized by the procedure below. The growth media was DMEe (Dulbecco's Modified Eagles Media) low glucose (Irvine Scientific), supplemented with 10% fetal calf serum (Hyclone), and 2 mM 1-glutamine (Irvine Scientific). The used media was growth media from a three day culture of 653.1 cells, centrifuged and filtered to remove cells. The CHAT Media (Conditioned Hypoxanthine Aminoptherin and Thymidine Media) was 50% growth media and 50% conditioned media with 100 units/ml of penicillin-streptomycin solution (irvine Scientific), $4 \times 10^{-7}$ M aminopterin (Sigma), $1 \times 10^{-4}$ M hypoxanthine (MA Bioproducts), $1.6 \times 10^{-5}$ M thymidine (MA Bioproducts), and 10 units/ml insulin (Eli Lily). The conditioned media was 50% growth media-50% used media and $2.5 \times 10^{-5}$ M b-mercaptoethanol (Sigma). Polyethylene glycol (PEG) with a molecular weight between about 1300 and 1600 (Sigma) was used. The injection media was DME low glucose with 100 units/ml penicillin-streptomycin solution. One-half milliliter of Pristane (2,6,10,14-tetramethylpentadecane, available from Aldrich) was injected intraperitoneally into each Balb/c mouse two weeks prior to hybridoma injection.

The hybridomas were made using the method developed by Kohler and Milstein, *Nature* 256:495 (1975). The spleen from the immunized mouse was aseptically removed after cervical dislocation and was ground in a tissue sieve until a single-cell suspension was obtained. After washing, the cells were mixed with the washed 653.1 myeloma cells in a 2:1 ratio of spleen to myeloma cells and then pelleted. The supernatant was removed and the PEG added slowly over one minute. PBS was added to bring the total volume to 22 ml and the cells were then pelleted for 8 minutes after the start of PEG addition. The pellet was resuspended in 200 ml of CHAT media and 0.2 ml of the suspension was added to each well of ten 96-well microtiter plates. The wells were supplied with fresh CHAT on days 6 and 7 post fusion.

Testing of the wells for growth using radioimmunoassay (RIA) began on day 10 and continued over the next 3–4 days. Wells with a count greater than the negative control were retested on the following day. If the reading remained greater than the negative control on the second day of testing, the colony was considered positive and was cloned. Cloning was carried out by limiting dilution in conditioned media into two 96-well plates, one with 5 cell/well and one plate with 1 cell/well. One week after cloning, single colony wells were tested by RIA. If all wells tested positive, the line was considered pure and was recloned a second time for stability. If all the wells did not test 100% positive, a positive well was used for the second cloning. The plates were tested again 7 days after the cloning. This procedure was repeated until all the clones tested 100% positive. The cells were then expanded in growth media and injected in injection media into the peritoneal cavity of Pristane-primed Balb/c mice at a concentration of about $3 \times 10^6$ hybridoma cells per mouse.

Prior to injection, supernatant from the cultured cells was used for isotyping by the Ouchterlony gel diffusion method, *Acta Path Microbiol Scand* 26:507 (1949). Ascites fluid was harvested from the mice about 10 days after the mice had been injected with the hybridoma cells. The ascites fluid was then titered by RIA and the IgG isotype content was measured using a Beckman ICS rate nephelometer.

The immunization protocol for generation of Gent 3B1 monoclonal antibody was as follows. A female Balb/c mouse was injected intraperitoneally with 20 μg of the gentamicin BSA antigen in Freund's complete. One month later, 20 μg of gentamicin BSA was injected intravenously. Two weeks after that, 20 μg of gentamicin BSA was given in a combination of intravenous and intraperitoneal injection. Three days thereafter, the immunized mouse's spleen was removed and fusion was performed. The hybridomas so prepared were capable of producing monoclonal antibody with a specific affinity for gentamicin.

The immunization protocol for generation of GV AS5 monclonal antibody was as follows. A female Balb/c mouse was injected intravenously with 1 μg of the gentamicin BSA antigen in Freund's complete. On day three, the mouse was injected with 139 μg of gentamicin BSA intravenously. On day four, the mouse was injected with 130 μg of gentamicin BSA intravenously. On day five, 139 μg of the gentamicin was injected intravenously. On day six, 139 μg of the gentamicin was again injected intravenously. On day seven, the immunized mouse's spleen was removed and fusion was carried out. The hybridomas so prepared were capable of producing monoclonal antibody with a specific affinity for gentamicin.

Two different monoclonal antibodies against gentamicin were prepared because gentamicin exists in several similar but not identical chemical species. Thus, an assay against gentamicin that uses monoclonal antibodies against two species of gentamicin permits a more accurate quantification of the amount of total gentamicin present.

Example 2

Detection of Gentamicin

An initial rate turbidimetric immunoassay was carried out to detect gentamicin in undiluted serum samples as follows. Two vials of ascites fluid were obtained by following the procedure of Example 1. One vial contained a solution of the monoclonal antibodies Gent 3B1, while the other vial of ascites fluid contained the monoclonal antibodies GV AS5.

Each vial of ascites fluid was centrifuged at 10 g. for 30 minutes at 4° C. One ml of supernatant was then removed from each vial and each 1 ml of ascites fluid was combined with 3 ml of a diluent. The diluent used was a Beckman ICS™ protein diluent, part #6637630. The same diluent was used in all the initial rate immunoassay Examples set forth below. The two 4 ml containers of diluted ascites fluid were combined to obtain 8 ml of fluid consisting of 2 ml of ascites fluid in 6 ml of diluent.

The diluted ascites fluid containing the two anti-Gentamicin monoclonal antibodies was then filtered through a 0.45μ low protein binding filter (Baxter; Acrodisc, part #F3057-3). Four ml of the filtered fluid was put into compartment C of a Synchron CX® 5 clinical analyzer cartridge. The Synchron CX® 5 is available from Beckman Instruments, Inc., Fullerton, Calif. as part #759300.

A running buffer was prepared by combining 60 ml of a buffer with 40 ml of the diluent. The buffer used was a Beckman ICS™ protein buffer, part #663600. The same buffer was used in all the initial rate immunoassay Examples set forth below. The 100 ml of running buffer prepared was put into compartment A of the Synchron CX® 5 clinical analyzer cartridge.

A gentamicin-bidentate conjugate was prepared in accordance with the protocol disclosed in U.S. Pat. No. 5,196,351, modified for the specific conjugate desired. The bidentate conjugate was then combined with avidin, thereby binding the biotin portion of the conjugate to the avidin. The resulting conjugate was diluted in the diluent to a concentration of 0.30 mg of conjugate per ml of diluent. Ten ml of the diluted conjugate was placed in compartment B of the Synchron CX® 5.

At time zero, 24 μl of the monoclonal antibodies in compartment C was aspirated by the Synchron® 5 clinical analyzer and added to a cuvette with 230 μl of the running buffer. The cuvette is a small substantially optically transparent container or vial. At time zero plus 320 seconds, 8 μl of an undiluted, gentamicin-containing serum sample was added to the cuvette.

At time zero plus 368 seconds, 28 μl of the gentamicin-bidentate conjugate from compartment B was added to the cuvette. At time zero plus 374 seconds (8 seconds after addition of conjugate), until time plus 406 seconds (32 seconds after addition of conjugate) the rate of increasing turbidity of the liquid medium in the cuvette was measured. Thus, the rate of increasing turbidity of the liquid medium was followed for a total of 24 seconds. The rate of increasing liquid medium turbidity is preferably not read until about 8 seconds after addition of conjugate to the cuvette, in order to allow the conjugate time to settle into the cuvette solution mixture. We have found that commencement of the turbidity measurement can occur immediately upon addition of conjugate (i.e. time zero plus 368 seconds in this Example) without undue negative influence on the accuracy of the drug quantification result by the present initial rate method. Preferably though, when a competitive inhibition immunoprecipitation reaction is initiated, a brief waiting period of several seconds is allowed to elapse before beginning rate signal measurement, as noted above. Comparison of this rate with a standard rate curve for gentamicin allowed quantification of the amount of gentamicin present.

FIG. 1 is a graph of a gentamicin assay carried out as set forth above. Each data point shown is from a photometric reading taken by the Synchron CX® 5 clinical analyzer at one second intervals. Thus, eight readings are taken over eight seconds. The instrument then pauses for eight seconds before taking another eight readings. The eight seconds on, eight seconds off nature of the data capture by the instrument, causes the apparent clustering of the data points.

The vertical axis of FIG. 1 shows cuvette solution turbidity as measured in milliabsorbance (mabs) units at 340 nm, flash corrected at 700 nm. The horizontal axis of FIG. 1 shows the elapse of time. FIG. 1 shows that from time zero to time zero plus 320 seconds there is a measurable cuvette sample turbidity due to the presence of the buffered anti-Gentamicin monoclonal antibody. This is referred to as a "reagent blank" turbidity. From time zero plus 320 seconds to time zero plus 368 seconds a higher level of solution turbidity is read due to addition of the analyte sample at time zero plus 320 seconds. It is important to note that the turbidity observed from time zero to time zero plus 320 seconds, and from time zero plus 320 seconds to time zero plus 368 seconds does not change over time; in other words there is no rate of turbidity change to be detected at these times.

At time zero plus 368 seconds the conjugate was added. An essentially immediate, substantially linear-with-time rate of change of the cuvette liquid medium turbidity was detected. Additionally, the initial and substantially linear rate signal of turbidity change occurs as the maximum rate signal of turbidity increase for this analyte detection method, due in part to the excess of anti-gentamicin antibody to gentamicin conjugate present in the cuvette liquid medium.

Example 3

Preparation of a Gentamicin Calibration Curve

The same Synchron CX® 5 clinical analyzer set forth in Example 2 was used. The same reagents were loaded into compartments A, B, and C of the instrument cartridge. Instead of using 8 µl of a gentamicin containing sample, six calibrators with known amounts of gentamicin (0, 1, 2, 4, 8, and 12 µg per ml) were used.

The rate of change of the cuvette liquid medium turbidity over time upon addition of conjugate was measured for each calibrator. The rate signals were plotted on a vertical axis against the gentamicin concentrations of the calibrators on the horizontal axis, as shown by FIG. 2. Automatic comparison by the Synchron CX® 5 clinical analyzer of such calibration values obtained, with the initial rate of change of cuvette liquid medium turbidity caused by an unknown amount of gentamicin in a sample, permitted detection and quantification of the amount of gentamicin present per unit volume of the physiological fluid sample.

Example 4

Determination of the Accuracy of the Gentamicin Assay

To determine the accuracy of the amount of gentamicin measured by the present initial rate method, a correlation plot was established using common regression analysis techniques. The gentamicin levels of forty six patient serum samples were measured by both the present initial rate method, as set forth by Example 2 above, and by fluorescent polarization immunoassay (FPIA, using an Abbott TDX™ Analyzer with Dade TDM (Therapeutic Drug Monitoring) controls, available from Baxter Scientific as part numbers B5700-2 (low), B5700-3 (mid-range), and B5700-4 (high control)).

The results are shown plotted on FIG. 3, with the calculated regression line which is defined by the function y=1.0139x−0.3288. The proximity of the gentamicin values assayed by the initial rate turbidimetric method to the regression line show the high accuracy and dependability of the present invention.

Reproducible gentamicin detection and quantification results were obtained by the initial rate method over a range of 0.1µg to 12 µg gentamicin per ml of serum. Within-run assay precision yielded coefficients of variation of 7.1%, 2.0%, and 2.0% at gentamicin concentrations of 1.2, 6.2, and 8.8 µg/ml of serum respectively. Between-run coefficients of variation were 11.7%, 2.5%, and 5.6% at the same levels.

Example 5

Preparation of Goat Anti-IgM Polyclonal Antibody

Goat anti-IgM polyclonal antibody was prepared as follows. Four goats were each injected with 25 µg of IgM emulsified in 3 ml Freund's complete adjuvant. For each goat, 0.5 ml was injected into each of two legs intravenously, and the remaining 2.0 ml was injected into 10 different sites via subcutaneous injection.

Twenty-eight days later, each goat was again injected with 25 µg of IgM emulsified in 3 ml Freund's complete adjuvant. One half of one ml was injected into each of two legs per goat by intravenous administration, and the remaining 2.0 ml was injected into 10 different sites via subcutaneous injection.

Second and third boosts were given at 8 weeks and 12 weeks respectively after the initial immunization of day 1. The injection at plus 8 weeks and plus 12 weeks were of 25 µg of IgM emulsified in Freund's complete adjuvant. All injections were carried out subcutaneously through a minimum of 15 different skin sites per goat.

At 14 weeks after the initial immunization, samples of blood from each goat were removed and titered for Anti-IgM content.

Example 6

Detection and Quantification of IgM

An initial rate turbidimetric immunoassay method was carried out to detect and quantify IgM in undiluted serum samples as follows. Goat anti-IgM prepared by the procedure of Example 5 was used. This antibody can also be purchased as Beckman part #449520.

One ml of the goat serum containing the anti-IgM polyclonal antibody was diluted in 2 ml of diluent and was placed in compartment B of the Synchron CX® 5 clinical analyzer cartridge.

The running buffer was prepared by mixing 60 ml of the buffer with 40 ml of the diluent. The 100 ml of running buffer was put into compartment A of the Synchron CX® 5 clinical analyzer cartridge.

At time zero, 200 µl of the running buffer in compartment A was combined in a cuvette with 70 µl of the Anti-IgM antibody from compartment B. At time zero plus 320 seconds, 3 µl of undiluted human serum sample containing IgM was also added to the cuvette.

An essentially immediate, substantially linear-with-time rate of change of the cuvette liquid medium turbidity was then detected. The initial rate of increasing cuvette liquid medium turbidity was measured by the instrument at 340 nm (flash corrected at 700 nm) from time zero plus 320 seconds to time zero plus 344 seconds (i.e. a 24 second initial rate measurement). It was determined that the rate measurement window can be read from time zero plus 320 seconds to time zero plus 336 seconds (i.e. a 16 second initial rate measurement window or signal detection period) with essentially the same results.

FIG. 4 shows the results of a turbidimetric immunoassay carried out by the initial rate method. A correlation curve to quantify the amount of IgM present in the serum sample was established in the same manner as in Example 3, substituting the appropriate commercially available IgM calibrators for the gentamicin calibrators.

FIG. 5 shows the results of a regression analysis obtained using the initial rate method for detecting and quantifying serum IgM and an Array® 360 (nephelometric) instrument method (Beckman, Array® Protein System Analyzer, part #757100). Eighty-three different human serum samples were assessed for IgM content by the initial rate method and again on the same samples, using the standard Array quantification method. As shown by FIG. 5, the proximity of the IgM values assayed by the initial rate turbidimetric method to the regression line show the high accuracy and dependability of the present invention. The regression line is defined by the function $y=0.8907x+11.8158$.

Example 7

Detection and Quantification of Valproic Acid

An initial rate turbidimetric immunoassay method was carried out to detect and quantify valproic acid in undiluted serum samples as follows. Goat anti-valproic acid polyclonal antibody was prepared by the procedure of Example 5, modified for the specific antibody desired.

One ml of the goat serum containing the antivalproic acid polyclonal antibody was diluted in 2 ml of diluent and was placed in compartment C of the Synchron CX® 5 clinical analyzer cartridge.

The running buffer was prepared by mixing 40 ml of the buffer with 5 ml of the diluent. The 45 ml of running buffer was put into compartment A of the Synchron CX® 5 clinical analyzer cartridge.

A valproic acid-bidentate conjugate was prepared following the procedure described in Example 2, and was diluted in diluent to a concentration of 0.40 mg of conjugate per ml of diluent. Ten ml of the diluted conjugate was placed in compartment B of the Synchron CX® 5 clinical analyzer cartridge.

At time zero, 40 µl of the polyclonal antibody solution in compartment C was added to a cuvette with 225 µl of the running buffer. At time zero plus 320 seconds, 3 µl of an undiluted, valproic acid-containing serum sample was added to the cuvette.

At time zero plus 336 seconds, 45 µl of the valproic acid-bidentate conjugate from compartment B was added to the cuvette. An essentially immediate, substantially linear-with-time rate of change of the cuvette liquid medium turbidity was then detected. At time zero plus 352 seconds (16 seconds after addition of conjugate), until time zero plus 384 seconds (48 seconds after addition of conjugate) the initial rate of increasing turbidity of the solution in the cuvette was measured. Comparison of this rate with a standard rate curve for valproic acid allowed for quantification of the amount of valproic acid present.

FIG. 6 is a graph of a valproic acid assay carried out as set forth above with the Synchron CX® 5 clinical analyzer. The vertical axis of FIG. 6 shows cuvette solution turbidity as measured in milliabsorbance (mabs) units at 340 nm, flash corrected at 700 nm. The horizontal axis of FIG. 6 shows time. At time zero plus 336 seconds the conjugate was added. An immediate, substantially linear-with-time rate of change of cuvette solution turbidity is evident. Additionally, the initial and substantially linear rate of turbidity change occurs as the maximum rate of turbidity increase for this analyte detection procedure due at least in part to the excess of anti-valproic acid antibody to valproic acid conjugate present in the cuvette liquid medium.

Valproic acid calibration and regression analysis was carried out as set forth previously for gentamicin in Examples 3 and 4 respectively, using appropriate calibrators with known amounts of valproic acid. For the valproic acid regression curve, the serum valproic acid levels of 72 patients were measured by both the initial rate method and by fluorescent polarization immunoassay. The proximity of the valproic acid values assayed by the initial rate turbidimetric method to the regression line showed the high accuracy and dependability of the present invention.

Example 8

Detection and Quantification of Haptoglobin

An initial rate turbidimetric immunoassay method was carried out to detect and quantify haptoglobin in undiluted serum samples as follows. Goat antihaptoglobin polyclonal antibody was prepared by the procedure of Example 5, modified for the specific antibody desired.

One ml of the goat serum containing the antihaptoglobin polyclonal antibody was diluted in 1 ml of diluent and placed in compartment C of the Synchron CX® 5 clinical analyzer cartridge.

The running buffer was prepared by mixing 150 ml of the buffer with 300 ml of the diluent. One hundred ml of this running buffer was put into compartment A of the Synchron CX® 5 clinical analyzer cartridge.

At time zero, 50 µl of the polyclonal antibody solution in compartment C was added to a cuvette with 225 µl of the running buffer from compartment A. At time zero plus 320 seconds, 3 µl of an undiluted, haptoglobin-containing human serum sample was added to the cuvette. An essentially immediate, substantially linear-with-time rate of change of the cuvette liquid medium turbidity was then detected.

From time zero plus 336 to time zero plus 360 seconds (from 16 to 40 seconds after addition of the serum sample) the initial rate of increasing turbidity of the solution in the cuvette was measured. This initial rate assay was also carried out with the rate of increasing turbidity of the solution in the cuvette being measured from time zero plus 320 seconds to time zero plus 344 seconds (from zero to 24 seconds after addition of analyte sample) with essentially the same haptoglobin quantification results. Comparison of these turbidity increase rates with a calibration curve for haptoglobin allowed for quantification of the amount of haptoglobin present.

FIG. 7 is a graph of a haptoglobin assay carried out as set forth above with the Synchron CX® 5 clinical analyzer. The vertical axis of FIG. 7 shows cuvette solution turbidity as measured in milliabsorbance (mabs) units at 340 nm, flash corrected at 700 nm. The horizontal axis of FIG. 7 shows time. At time zero plus 320 the 3 µml of haptoglobin-containing sample was added. An immediate substantially linear-with-time rate of change of cuvette solution turbidity is evident. Additionally, the initial and substantially linear rate of turbidity change occurs as the maximum rate of turbidity increase due at least in part to the excess of anti-haptoglobin antibody to haptoglobin present in the cuvette liquid medium.

A haptoglobin calibration curve was prepared as previously set forth using appropriate calibrators with known amounts of haptoglobin. A haptoglobin regression analysis was also carried out by comparing the haptoglobin quantification results obtained upon fifty human serum samples by the initial rate method with the haptoglobin quantification results obtained on the same samples on the Array® instrument. The proximity of the haptoglobin values assayed by the initial rate turbidimetric method to the regression line showed the high accuracy and dependability of the present invention.

Example 9

Detection and Quantification of Phenobarbital

An initial rate turbidimetric immunoassay method was carried out to detect and quantify phenobarbital in undiluted serum samples as follows. Mouse ascites fluid containing monoclonal antibody against phenobarbital was obtained following the procedure of Example 1, modified for the specific monoclonal antibody desired, except that a combination of two different monoclonal antibodies was not used for the phenobarbital immunoassay, as it was used with the gentamicin immunoassay by the initial rate method.

A vial of the ascites fluid was centrifuged at 10 g. for 30 minutes at 4° C. One ml of supernatant was then removed from the vial and combined with 2 ml of the diluent.

The diluted ascites fluid containing the antiphenobarbital monoclonal antibodies was then filtered through a 0.45∞ low protein binding filter (Baxter; Acrodisc, part #F3057-3). The three ml of filtered fluid was put into compartment C of the Synchron CX® 5 clinical analyzer cartridge.

The running buffer was prepared by mixing 40 ml of the buffer with 10 ml of the diluent. The 50 ml of running buffer was put into compartment A of the Synchron CX® 5 clinical analyzer cartridge.

A phenobarbital-bidentate conjugate was prepared following the procedure described in Example 2, and was diluted in diluent to a concentration of 0.50 mg of conjugate per ml of diluent. Ten ml of the diluted conjugate was placed in compartment B of the Synchron CX® 5 clinical analyzer cartridge.

At time zero, 36 µl of the monoclonal antibody solution in compartment C was added to a cuvette with 200 µl of the running buffer from compartment A. At time zero plus 320 seconds, 3 µl of an undiluted, phenobarbital-containing serum sample was added to the cuvette.

At time zero plus 336 seconds, 32 µl of the phenobarbital-bidentate conjugate from compartment B was added to the cuvette. An essentially immediate, substantially linear-with-time rate of change of the cuvette liquid medium turbidity was then detected. At time zero plus 360 seconds (24 seconds after addition of conjugate), until time zero plus 396 seconds (60 seconds after addition of conjugate) the initial rate of increasing turbidity of the solution in the cuvette was measured. Comparison of this rate with a calibration for phenobarbital allowed for quantification of the amount of phenobarbital present.

Phenobarbital calibration and regression analyses were carried out as set forth previously for gentamicin in Examples 3 and 4 respectively, using appropriate calibrators with known amounts of phenobarbital. For the phenobarbital regression analysis, the serum phenobarbital levels of multiple patients were measured by both the initial rate method and a latex-based immunoassay method. The proximity of the phenobarbital values assayed by the initial rate turbidimetric method to the regression line showed the high accuracy and dependability of the present invention.

Example 10

Detection and Quantification of Theophylline

An initial rate turbidimetric immunoassay method was carried out to detect and quantify theophylline in undiluted serum samples as follows. Mouse ascites fluid containing monoclonal antibody against theophylline was obtained following the procedure of Example 1, modified for the specific monoclonal antibody desired, except that a combination of two different monoclonal antibodies was not used for the theophylline immunoassay, as it was used with the gentamicin immunoassay procedure by the initial rate method.

A vial of the ascites fluid was centrifuged at 10 g. for 30 minutes at 4° C. One ml of supernatant was then removed from the vial and combined with 2.50 ml of the diluent.

The diluted ascites fluid containing the antitheophylline monoclonal antibodies was then filtered through a 0.45µ low protein binding filter (Baxter; Acrodisc, part #F3057-3). Four ml of the filtered fluid was put into compartment C of the Synchron CX® 5 clinical analyzer cartridge.

The running buffer was prepared by mixing 30 ml of the buffer with 20 ml of the diluent. The 50 ml of running buffer was put into compartment A of the Synchron CX® 5 clinical analyzer cartridge.

A theophylline-bidentate conjugate prepared following the procedure described in Example 2, and was diluted in diluent to a concentration of 0.524 mg of conjugate per ml of diluent. Ten ml of the diluted conjugate was placed in compartment B of the Synchron CX® 5 clinical analyzer cartridge.

At time zero, 45 µl of the monoclonal antibody solution in compartment C was added to a cuvette with 230 µl of the running buffer from compartment A. At time zero plus 320 seconds, 3 µl of an undiluted, theophylline-containing serum sample was added to the cuvette.

At time zero plus 336 seconds, 32 µl of the theophylline-bidentate conjugate from compartment B was added to the cuvette. An essentially immediate, substantially linear-with-time rate of change of the cuvette liquid medium turbidity was then detected. At time zero plus 360 seconds (24 seconds after addition of conjugate), until time zero plus 396 seconds (60 seconds after addition of conjugate) the initial rate of increasing turbidity of the solution in the cuvette was measured. Comparison of this initial rate with a calibration curve for theophylline allowed for quantification of the amount of theophylline present.

Theophylline calibration and regression analyses were carried out as set forth previously for gentamicin in Examples 3 and 4 respectively, using appropriate calibrators with known amounts of theophylline. The proximity of the theophylline values assayed by the initial rate turbidimetric method to the regression line showed the high accuracy and dependability of the present invention.

Example 11

Detection and Quantification of Procainamide

An initial rate turbidimetric immunoassay method was carried out to detect and quantify procainamide in undiluted serum samples as follows. Goat antiprocainamide polyclonal antibody was prepared by the procedure of Example 5, modified for the specific antibody desired.

One ml of the goat serum containing the antiprocainamide polyclonal antibody was diluted in 2 ml of diluent and was placed in compartment C of the Synchron CX® 5 clinical analyzer cartridge.

The running buffer was prepared by mixing 35 ml of the buffer with 10 ml of the diluent. The 45 ml of running buffer was put into compartment A of the Synchron CX® 5 clinical analyzer cartridge.

A procainamide-bidentate conjugate was prepared following the procedure described in Example 2, and was diluted in diluent to a concentration of 0.40 mg of conjugate per ml of diluent. Ten ml of the diluted conjugate was placed in compartment B of the Synchron CX® 5 clinical analyzer.

At time zero, 35 µl of the polyclonal antibody solution in compartment C was added to a cuvette with 225 µl of the running buffer from compartment A. At time zero plus 320 seconds, 10 µl of an undiluted, procainamide-containing serum sample was added to the cuvette.

At time zero plus 336 seconds, 45 μl of the procainamide-bidentate conjugate from compartment B was added to the cuvette. An essentially immediate, substantially linear-with-time rate of change of the cuvette liquid medium turbidity was then detected. At time zero plus 352 seconds (16 seconds are addition of conjugate), until time zero plus 388 seconds (52 seconds after addition of conjugate) the initial rate of increasing turbidity of the liquid medium in the cuvette was measured. Comparison of this rate with a calibration rate curve for procainamide allowed for quantification of the amount of procainamide present.

Procainamide calibration and regression analyses were carried out as set forth previously for gentamicin in Examples 3 and 4 respectively, using appropriate calibrators with known amounts of procainamide. For the procainamide regression analysis, the serum procainamide levels of 52 patients were measured by both the initial rate method and by fluorescent polarization immunoassay. The proximity of the procainamide values assayed by the initial rate turbidimetric method to the regression line showed the high accuracy and dependability of the present invention.

Example 12

Detection and Quantification of N-Acetyl Procainamide

An initial rate turbidimetric immunoassay method was carried out to detect and quantify serum N-acetyl procainamide in undiluted serum samples as follows. Goat anti-N-acetyl procainamide polyclonal antibody was prepared by the procedure of Example 5, modified for the specific antibody desired.

One ml of the goat serum containing the anti-N-acetyl procainamide polyclonal antibody was diluted in 2 ml of diluent and was placed in compartment C of the Synchron CX® 5 clinical analyzer cartridge.

The running buffer was prepared by mixing 40 ml of the buffer with 5 ml of the diluent. The 45 ml of running buffer was put into compartment A of the Synchron CX® 5 clinical analyzer cartridge.

An N-acetyl procainamide-bidentate conjugate was prepared following the procedure described in Example 2, and was diluted in diluent to a concentration of 0.40 mg of conjugate per ml of diluent. Ten ml of the diluted conjugate was placed in compartment B of the Synchron CX® 5 clinical analyzer cartridge.

At time zero, 45 μl of the polyclonal antibody solution in compartment B was added to a cuvette with 225 μl of the running buffer from compartment A. At time zero plus 320 seconds, 10 μl of an undiluted, N-acetyl procainamide-containing serum sample was added to the cuvette.

At time zero plus 336 seconds, 40 μl of the N-acetyl procainamide bidentate conjugate from compartment B was added to the cuvette. An essentially immediate, substantially linear-with-time rate of change of the cuvette liquid medium turbidity was then detected. At time zero plus 352 seconds (16 seconds after addition of conjugate), until time zero plus 388 seconds (52 seconds after addition of conjugate), the initial rate of increasing turbidity of the solution in the cuvette was measured. Comparison of this initial rate with a standard rate curve for N-acetyl procainamide allowed for quantification of the amount of N-acetyl procainamide present.

N-acetyl procainamide calibration and regression analyses were carried out as set forth previously for gentamicin in Examples 3 and 4 respectively, using appropriate calibrators with known amounts of N-acetyl procainamide. For the N-acetyl procainamide regression analysis, the serum N-acetyl procainamide levels of multiple patients were measured by both the initial rate method and by fluorescent polarization immunoassay. The proximity of the N-acetyl procainamide values assayed by the initial rate turbidimetric method to the regression line showed the high accuracy and dependability of the present invention.

Example 13

Detection and Quantification of IgG

An initial rate turbidimetric immunoassay method was carried out to detect and quantify IgG in undiluted serum samples. The antibody used was an anti-IgG polyclonal antibody prepared in accordance with the procedure of Example 5, modified for the specific antibody desired. The Synchron CX® 5 clinical analyzer was also used.

After combining the antibody and the serum sample in the liquid medium, an essentially immediate, substantially linear-with-time rate of change of the cuvette liquid medium turbidity was then detected. Cuvette solution turbidity was read from time zero to time zero plus 24 seconds after addition of an aliquot of the IgG-containing undiluted serum sample to a liquid medium in the cuvette.

IgG calibration and regression analyses were carried out as set forth previously for gentamicin in Examples 3 and 4 respectively, using appropriate calibrators with known amounts of IgG. For the IgG regression curve, the serum IgG levels of 57 patients were measured by both the initial rate method and by the Array® instrument upon the same 57 samples. The proximity of the IgG values assayed by the initial rate turbidimetric method to the regression line showed the high accuracy and dependability of the present invention.

Example 14

Detection and Quantification of IgA

An initial rate turbidimetric immunoassay method was carried out to detect and quantify IgA in undiluted serum samples. The antibody used was an anti-IgA polyclonal antibody prepared in accordance with the procedure of Example 5, modified for the specific antibody desired. The Synchron CX® 5 clinical analyzer was also used.

After combining the antibody and the serum sample in the liquid medium, an essentially immediate, substantially linear-with-time rate of change of the cuvette liquid medium turbidity was then detected. Cuvette solution turbidity was read from time zero to time zero plus 24 seconds after addition of an aliquot of the IgA-containing undiluted serum sample.

IgA calibration and regression analyses were carried out as set forth previously for gentamicin in Examples 3 and 4 respectively, using appropriate calibrators with known amounts of IgA. For the IgA regression curve, the serum IgA levels of 54 patients were measured by both the initial rate method and by the Array® instrument upon the same 54 samples. The proximity of the IgA values assayed by the initial rate turbidimetric method to the regression line showed the high accuracy and dependability of the present invention.

Example 15

Detection and Quantification of C3

An initial rate turbidimetric immunoassay method was carried out to detect and quantify the protein complement C3 in undiluted serum samples. The antibody used was an anti-C3 polyclonal antibody prepared in accordance with the procedure of Example 5, modified for the specific antibody desired. The Synchron CX® 5 clinical analyzer was also used.

After combining the antibody and the serum sample in the liquid medium, an essentially immediate, substantially linear-with-time rate of change of the cuvette liquid medium turbidity was then detected. Cuvette solution turbidity was read from time zero to time zero plus 24 seconds after addition of an aliquot of the C3-containing undiluted serum sample.

C3 calibration and regression analysis was carried out as set forth previously for gentamicin in Examples 3 and 4 respectively, using appropriate calibrators with known amounts of C3. For the C3 regression analysis, the serum C3 levels of 102 patients were measured by both the initial rate method and by the Array® instrument upon the same 102 samples. The proximity of the C3 values assayed by the initial rate turbidimetric method to the regression line showed the high accuracy and dependability of the present invention.

Example 16

Detection and Quantification of C4

An initial rate turbidimetric immunoassay method was carried out to detect and quantify the protein complement C4 in undiluted serum samples. The antibody used was an anti-C4 polyclonal antibody prepared in accordance with the procedure of Example 5, modified for the specific antibody desired. The Synchron CX® 5 clinical analyzer was also used.

After combining the antibody and the serum sample in the liquid medium, an essentially immediate, substantially linear-with-time rate of change of the cuvette liquid medium turbidity was then detected. Cuvette solution turbidity was read from time zero to time zero plus 24 seconds after addition of an aliquot of the C4-containing undiluted serum sample.

C4 calibration and regression analyses were carried out as set forth previously for gentamicin in Examples 3 and 4 respectively, using appropriate calibrators with known amounts of C4. For the C4 regression curve, the serum C4 levels of 99 patients were measured by both the initial rate method and by the Array® instrument upon the same 99 samples. The proximity of the C4 values assayed by the initial rate turbidimetric method to the regression line showed the high accuracy and dependability of the present invention.

Numerous other analytes have also been detected and quantified by the disclosed initial rate method. These additional analytes include transferrin, phenytoin (dilantin), CRP, tobramycin, carbamezapine, cocaine, amphetamine, metamphetamine, rheumatoid factors, and anti-streptolysin-O.

With each of these analytes, upon combining an anti-analyte antibody and the serum sample in the liquid medium, or upon combining the anti-analyte antibody and the analyte-conjugate in the liquid medium, an essentially immediate, substantially linear-with-time rate of change of the cuvette liquid medium turbidity occurred. This substantially constant-over-time initial rate signal was then detected using the Synchron CX® 5 clinical analyzer. Thus, the present initial rate method has been used to rapidly and accurately detect and quantify a wide diversity of analytes.

The initial rate photometric immunoassay method disclosed herein has many advantages, including the following:

1. The initial rate method is faster than either existing rate or end-point photometric methods because the initial rate of change of a photometric property is detected;

2. The initial rate method is as accurate as either existing rate or end-point photometric methods, and unlike the end-point methods, the method does not produce the extensive interfering signal obtained when undiluted physiological fluid samples are used in end-point methods;

3. The initial rate method can be practiced upon an undiluted sample of a physiological fluid such as, for example, serum, urine or cerebrospinal fluid;

4. The initial rate method permits detection of a substantially linear-with-time initial rate signal thereby significantly simplifying analyte detection and quantification;

5. The initial rate method permits detection of the substantially linear-with-time initial rate signal essentially immediately upon initiation of a photometrically detectable immunoprecipitation reaction, thereby significantly expediting analyte-containing sample analysis;

6. The initial rate method is very sensitive, being able to detect analyte concentrations at least as low as about 0.1 µg per ml of a physiological fluid; and 7. The initial rate method is easily adaptable to detection and quantification of a wide variety of biological molecules such as haptens, toxins, antigens, peptide hormones, steroids, vitamins, drugs (both therapeutic drugs and drugs of abuse) and metabolites and derivatives thereof, in diverse physiological fluids.

Although the present invention has been described in detail with regard to certain preferred methods, other embodiments, versions, and modifications within the scope of the present invention are possible. For example, a wide variety of conjugates can be used for hapten-analyte detection, and the particular buffer-diluent combinations and liquid medium additive concentrations are easily optimized according to the nature of the analyte of interest.

Furthermore, the initial rate invention can be used to detect and quantify numerous additional specific analytes such as pyrimidone, ethosuximide, lidocaine, vancomycin, acetaminophen, and cannabinol compounds including, tetrahydrocannabinol. Accordingly, the spirit and scope of the following claims should not be limited to the descriptions of the preferred embodiments set forth above.

We claim:

1. An initial rate photometric method for detecting a proteinaceous analyte with a suitable photometer comprising:

(1) a light source, and (2) a light detector, the method comprising the steps of:

(a) arranging the light detector in front of the light source, so that the light source and the light detector are aligned along substantially the same axis;

(b) interposing a substantially optically transparent container between the light detector and the light source;

(c) combining in a liquid medium in the container;

(A) a sample of an undiluted physiological fluid containing the proteinaceous analyte, and (B) an excess of an anti-analyte antibody to initiate a photometrically detectable immunoprecipitation reaction in the liquid medium;

(d) irradiating the liquid medium in the container with a light of a preselected wavelength from the light source;

(e) detecting the analyte by;

(i) commencing detection of a substantially constant initial rate of increasing turbidity of the liquid medium within a period of time that begins with the initiating step and ends about 20 seconds after the beginning of the initiating step, and (ii) terminating detection of the substantially constant initial rate of increasing turbidity of the liquid medium at a second later period of time less than about 60 seconds after the beginning of the initiating step, and (f) quantifying the amount of the analyte present per unit volume of the undiluted physiological fluid from the change in the turbidity of the liquid medium from step (e)(i) to step (e)(ii).

2. The method of claim 1, wherein commencing detection of the substantially constant initial rate of change of the photometric property of the liquid medium occurs within a period of time that begins with the initiating step and ends about 10 seconds after the beginning of the initiating step.

3. The method of claim 1, wherein terminating detection of the substantially constant initial rate of change of the photometric property of the liquid medium occurs within a period of time that begins with the initiating step and ends about 50 seconds after the beginning of the initiating step.

4. The method of claim 1, wherein terminating detection of the substantially constant initial rate of change of the photometric property of the liquid medium occurs within a period of time that begins with the initiating step and ends about 40 seconds after the beginning of the initiating step.

5. The method of claim 1, wherein terminating detection of the substantially constant initial rate of change of the photometric property of the liquid medium occurs within a period of time that begins with the initiating step and ends about 30 seconds after the beginning of the initiating step.

6. The method of claim 1, wherein terminating detection of the substantially constant initial rate of change of the photometric property of the liquid medium occurs within a period of time that begins with the initiating step and ends about 20 seconds after the beginning of the initiating step.

7. The method of claim 1, wherein the antibody for the analyte is selected from the group consisting of polyclonal antibodies and monoclonal antibodies.

8. The method of claim 1, wherein the antibody and the analyte are combined in the liquid medium in a ratio that is at least about 1.2:1.

* * * * *